United States Patent [19]

Baneth

[11] Patent Number: 5,603,065
[45] Date of Patent: Feb. 11, 1997

[54] HANDS-FREE INPUT DEVICE FOR OPERATING A COMPUTER HAVING MOUTHPIECE WITH PLURALITY OF CELLS AND A TRANSDUCER FOR CONVERTING SOUND INTO ELECTRICAL CONTROL SIGNALS

[76] Inventor: Robin C. Baneth, 523 Pace St., Raleigh, N.C. 27604-1957

[21] Appl. No.: 202,994

[22] Filed: Feb. 28, 1994

[51] Int. Cl.⁶ .............................. G06F 13/00; G06F 3/16
[52] U.S. Cl. .......................... 395/893; 395/2.8; 395/825; 395/882; 395/892; 340/407.2; 340/825; 340/825.19; 340/825.25
[58] Field of Search .......................... 364/709.11, 708.1, 364/400; 84/377, 723; 307/117; 381/36; 340/407.2, 825, 825.19, 825.25; 395/2.8, 825, 882, 892, 893

[56] References Cited

U.S. PATENT DOCUMENTS

| | | | |
|---|---|---|---|
| 3,582,671 | 6/1971 | Ott | 307/117 |
| 4,085,646 | 4/1978 | Naumann | 84/1.09 |
| 4,385,541 | 5/1983 | Muller et al. | 84/1.14 |
| 4,476,554 | 10/1984 | Smith et al. | 367/197 |
| 4,527,456 | 7/1985 | Perkins et al. | 84/1.04 |
| 4,566,363 | 1/1986 | Arai | 84/1.08 |
| 4,595,990 | 6/1986 | Garwin et al. | 364/518 |
| 4,619,175 | 10/1986 | Matsuzaki | 84/1.01 |
| 4,856,066 | 8/1989 | Lemelson | 381/36 |
| 4,984,499 | 1/1991 | Schille | 84/734 |
| 5,142,961 | 9/1992 | Paroutaud | 84/726 |
| 5,171,930 | 12/1992 | Teaney | 84/725 |
| 5,245,130 | 9/1993 | Wheaton | 84/742 |
| 5,305,244 | 4/1994 | Newman et al. | 364/708.1 |

FOREIGN PATENT DOCUMENTS

| | | |
|---|---|---|
| 61-269722 | 11/1986 | Japan. |
| 04-328600 | 11/1992 | Japan. |

OTHER PUBLICATIONS

IBM Technical Disclosure Bulletin, vol. 28 No. 4, Sep. 1985, p. 1605.
IBM Technical Disclosure Bulletin, vol. 28 No. 11, Apr. 1986, p. 4763.

*Primary Examiner*—Thomas C. Lee
*Assistant Examiner*—Po C. Huang
*Attorney, Agent, or Firm*—Rhodes, Coats & Bennett, L.L.P.

[57] ABSTRACT

An input device for a computer includes a mouthpiece and a interface for coupling the mouthpiece to the computer. The mouthpiece includes a plurality of air cells arranged in rows for entering commands to the computer. The are each assigned a command and a chosen command can be entered by inhaling or exhaling through the corresponding cell. The interface identifies which cell a user has selected and produces a distinct digital signal corresponding to that cell. In the preferred embodiment, a MIDI interface is used which discriminates between the different sounds produced by each cell. An on-screen keyboard is selectively displayed on the display screen of the computer to aid a user in selecting and entering commands into the computer. Software allows the user to interact and control different programs loaded on the computer. Potential users include the physically-challenged, astronauts, SCUBA divers, surgeons, construction workers, and musicians.

18 Claims, 8 Drawing Sheets

HANDS-FREE INPUT DEVICE FOR OPERATING A COMPUTER HAVING MOUTHPIECE WITH PLURALITY OF CELLS AND A TRANSDUCER FOR CONVERTING SOUND INTO ELECTRICAL CONTROL SIGNALS

FIELD OF THE INVENTION

The present invention relates generally to computer systems and more particularly to an input device for a computer in which data and commands are input by aspiration (i.e. blowing or sucking).

BACKGROUND OF THE INVENTION

Approximately 20 million people within the United States have some form of mobility impairment. Movement disabilities can result from strokes, accidents, severe arthritis, neuromuscular disfunctions, deformity, amputation, paralysis, spinal problems, and cumulative trauma disorders. In addition, repetitive motion disorders from prolonged keyboard use, such as carpal tunnel syndrome can result in inability to perform one's job. In the past, these people have been largely excluded or displaced from the work force resulting in a tremendous loss of productivity. The exclusion of physically challenged persons from the work force is largely a result of high accommodation costs and the perceived inability of such persons to compete effectively in the work force.

With adaptive devices, it is possible to integrate movement physically-challenged persons into the work force, and to provide a greater degree of independence for such persons. In particular, the use of computers in combination with adaptive devices, can remove many of the barriers that physically-challenged people face. For example, telecomputing enables persons to work at home using computers. With adaptive devices, persons with severe paralysis can operate computers. However, adaptive devices currently in use have several drawbacks. The relatively high expense of adaptive devices make computers adapted to serve the physically challenged more expensive than computers used by physically-challenged persons. Further, adaptive devices which have been used in the past do not enable motor impaired users to reach the same levels of efficiency as non-impaired users.

In the future, voice input technology may provide a viable substitute for computer keyboards. However, there may be circumstances where voice input technology may not be adequate. For example, users which cannot speak, or which cannot pronounce clearly would not benefit from a voice input technology. Additionally, the noise levels in the work environment or task complexity may make voice input technology unsuitable. For example, a worker may be engaged in communications while simultaneously performing a task. Critical task information might go unattended while an operator is speaking since it is difficult to vocalize and listen simultaneously. Also, it may be advantageous for workers in certain applications to hear certain external information, annunciators, audio alarms, command feedback, or task feedback. Missing auditory feedback is much less likely to occur when aspirating rather than talking.

Adaptive devices customarily used by physically-challenged persons may also have other applications. For example, there are certain environments where the hands-free operation of a computer might be desirable. For example, astronauts may need to operate a computer while making repairs to a space station or a spacecraft. Other potential users include SCUBA divers, construction workers, surgeons, and musicians.

Accordingly, there is a need for an input device that will enable hands-free operation of a computer by both physically-challenged and non-physically-challenged persons. The adaptive device should be relatively simple, low cost, and enable the physically-challenged user to approach the efficiency of non-physically-challenged users.

SUMMARY AND OBJECTS OF THE PRESENT INVENTION

The present invention is an input device for a computer system that allows hands-free control of a computer. Instead, a user enters commands and information into a computer by aspiration (i.e. blowing or sucking) into a device that resembles a harmonica. Because the mouth-actuated computer system of the present invention can be controlled completely by the use of the mouth, a movement impaired person and others needing a hands-free computer can effectively use a computer.

The input device of the present invention generally includes a mouthpiece, a computer, and an interface for operatively connecting the mouthpiece to the computer. The mouthpiece has a plurality of cells through which the user exhales or inhales to select and enter commands into the computer. The mouthpiece has a ergonomic shape to enable a user to easily access any of the cells.

In the preferred embodiment, a MIDI interface (musical instrument digital interface) is used for interfacing the mouthpiece with the computer. The MIDI interface converts sounds produced by each cell into digital signals. The MIDI interface identifies which cell was selected by the user because each cell is uniquely shaped to produce a distinct sound. The distinct sounds produced by exhaling or inhaling through the cells are converted to digital signals that can be interpreted by the computer or synthesizer.

To aid a user in selecting and entering commands, an on-screen keyboard is displayed on the computer display screen to provide visual feedback. The keyboard displays what characters and commands have been assigned to the cells of the mouthpiece. A user uses the on-screen keyboard to select and enter commands and information into the computer. Additionally, audio feedback can be used for vision impaired persons to announce the entry of commands and characters into the computer.

Accordingly, it is an object of the present invention to provide a hands-free input device for a computer system for use by physically challenged persons and non-physically challenged persons.

Another object of the present invention is to provide an input device for a computer that enables commands to be entered by blowing (exhaling) and/or sucking (inhaling) on a mouthpiece.

Another object of the present invention is to provide an input device of a computer that enables a movement-limited person to operate a computer more efficiently, Another object of the present invention is to provide an input device for a computer that has anthropometric design to provide for more effective entering of commands.

Other objects and advantages of the present invention will become apparent and obvious from a study of the following description and the accompanying drawings which are merely illustrative of such invention.

DETAILED DESCRIPTION OF THE PREFERRED EMBODIMENTS

Figure 1:
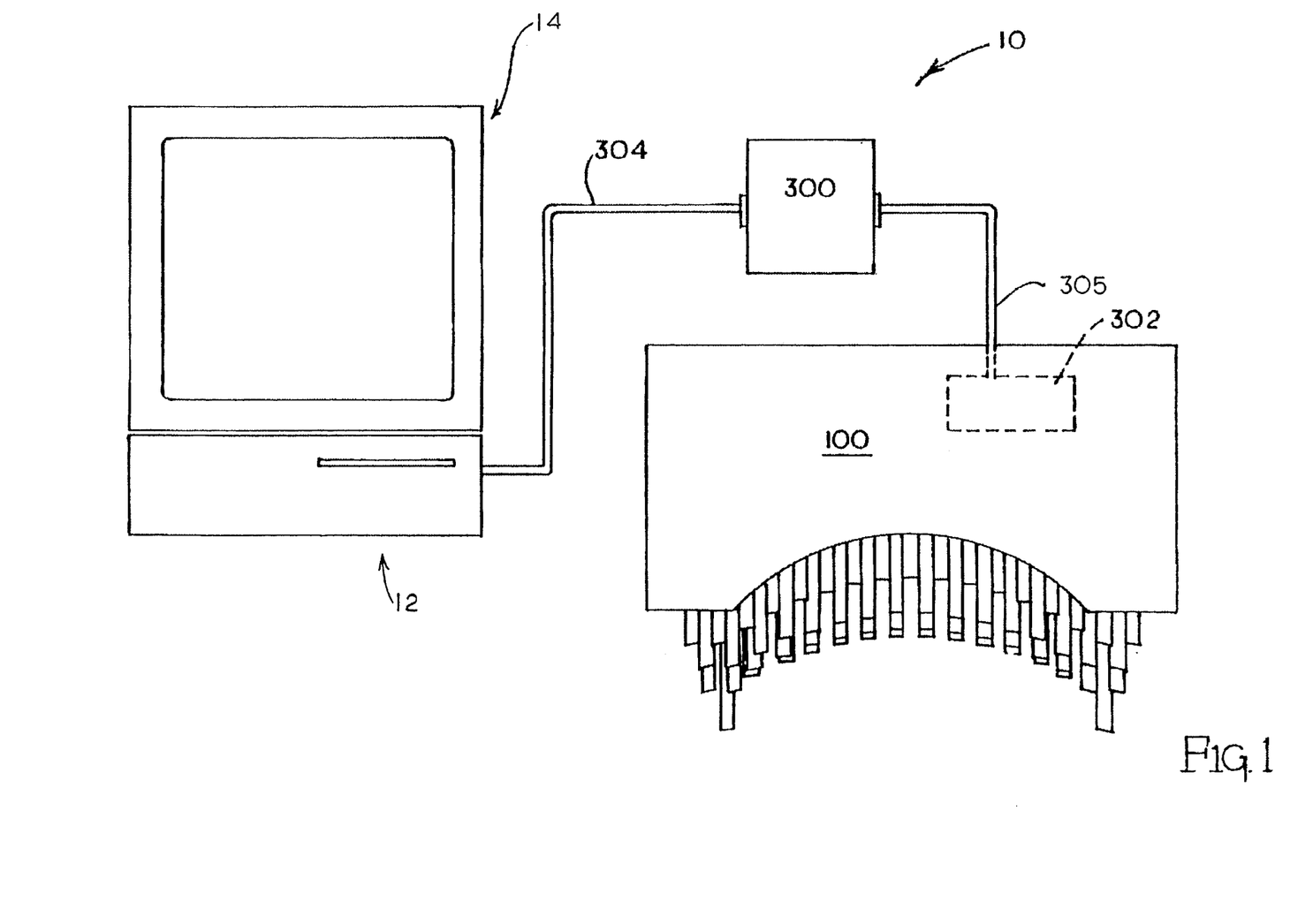
FIG. 1 is a schematic of the input device of the present invention.

With further reference to the drawings, the input device of the present invention is indicated generally by the numeral 10. Input device 10 allows hands-free interaction with a computer 12 by both handicapped and non-handicapped users. The computer 12 could be a conventional desktop computer as shown in FIG. 1. Alternately, the computer 12 could be specially designed to mount to the user's body. Also, the computer 12 could be mounted within the helmet of a protective suit, such as space suit or diver's suit, in which the faceplate functions as a heads-up display that could be alternately turned on and off with a single breath. Another alternative would be to incorporate the CPU and display with the input device 10 in a manner similar to a "lap-top" computer. Such a computer could be mounted to the user's shoulders by specifically designed mounts.

Input device 10 generally includes a mouthpiece 100 for entering commands to the computer 12, a mounting system 200 for mounting the mouthpiece 100, and a communications interface 300 that connects to the mouthpiece 100 and enables commands to be transmitted to and interpreted by the computer 12.

Figure 2:
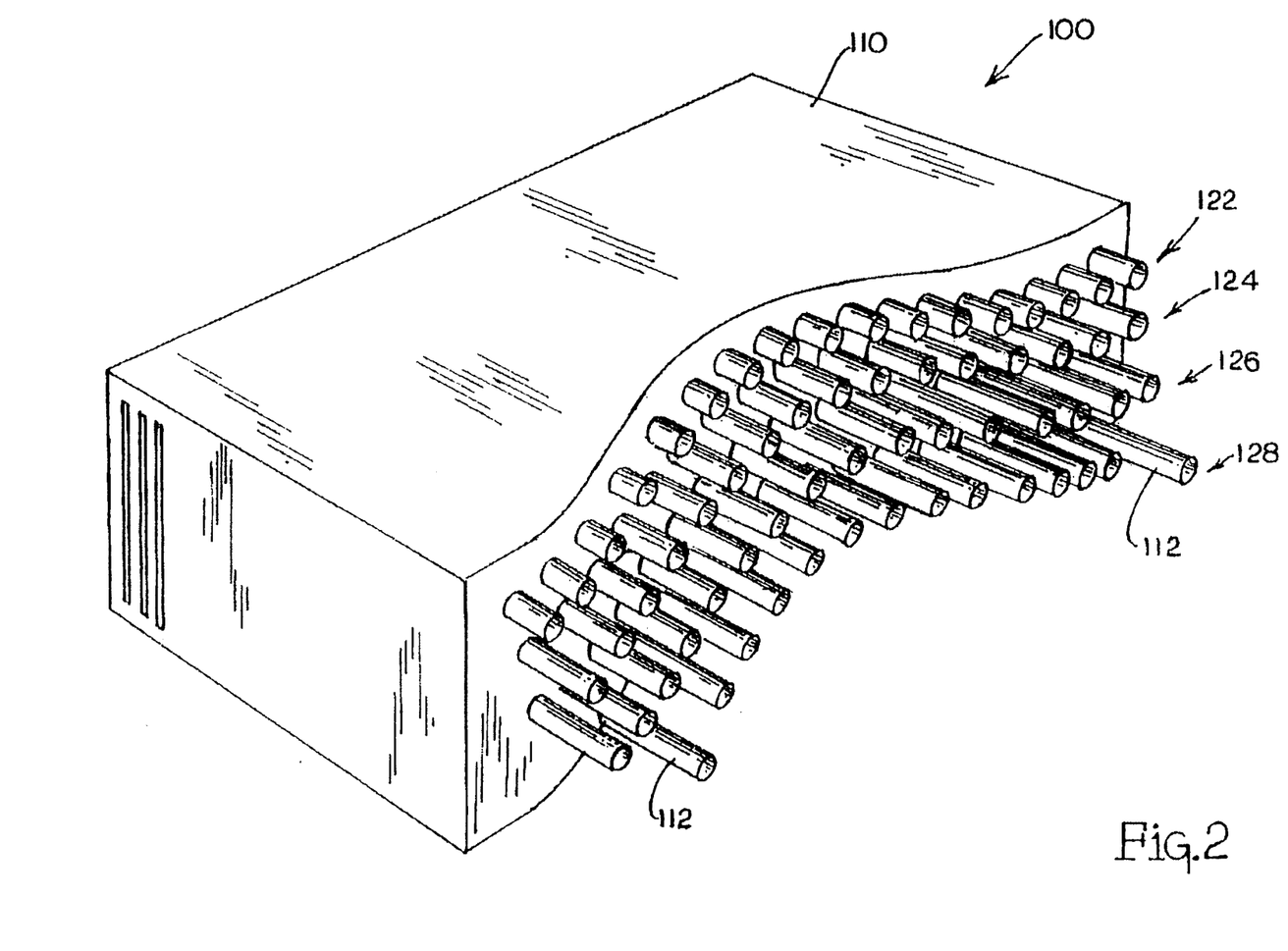
FIG. 2 is a perspective view of the mouthpiece.
Figure 3:
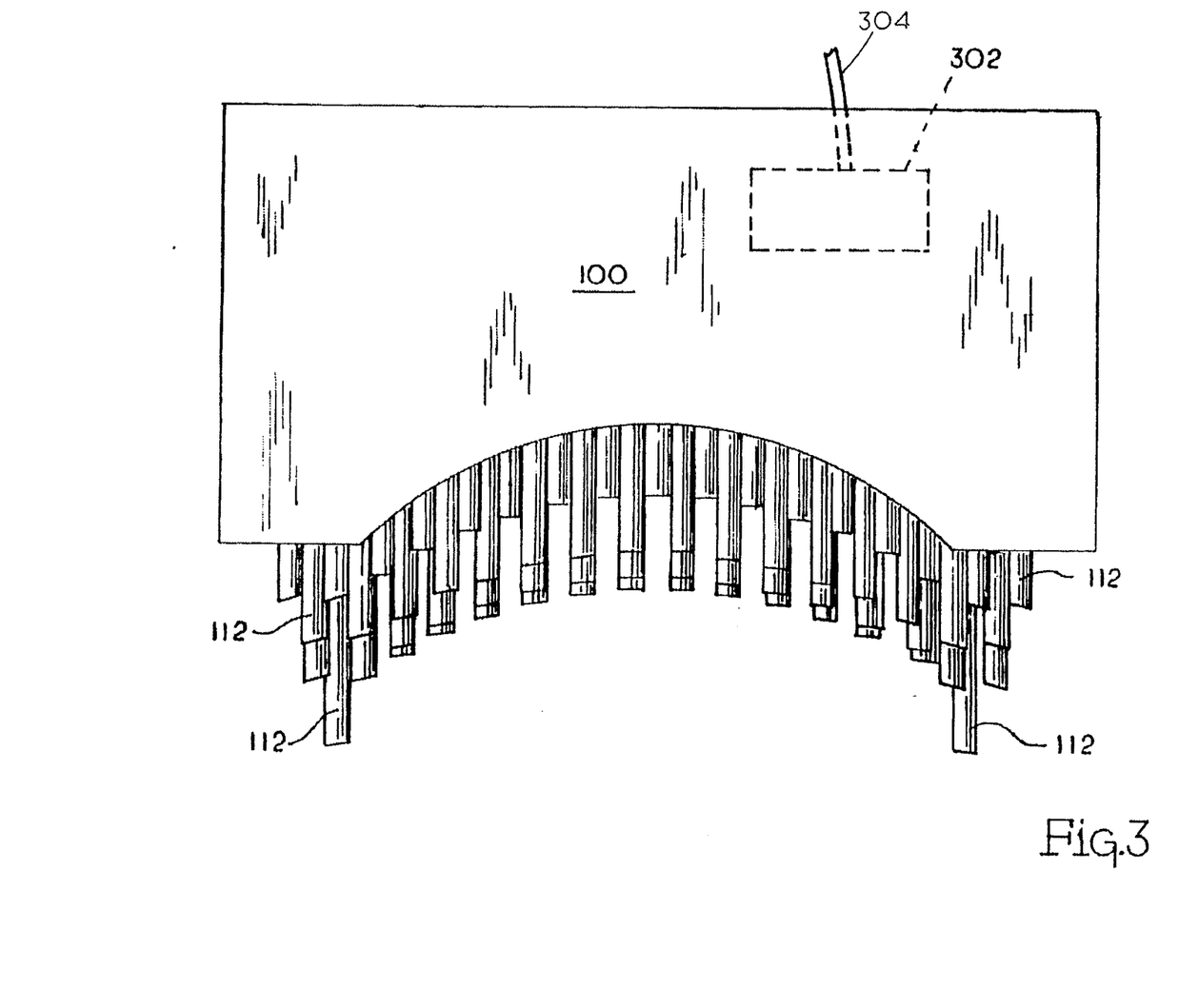
FIG. 3 is a top view of the mouthpiece.
Figure 4:
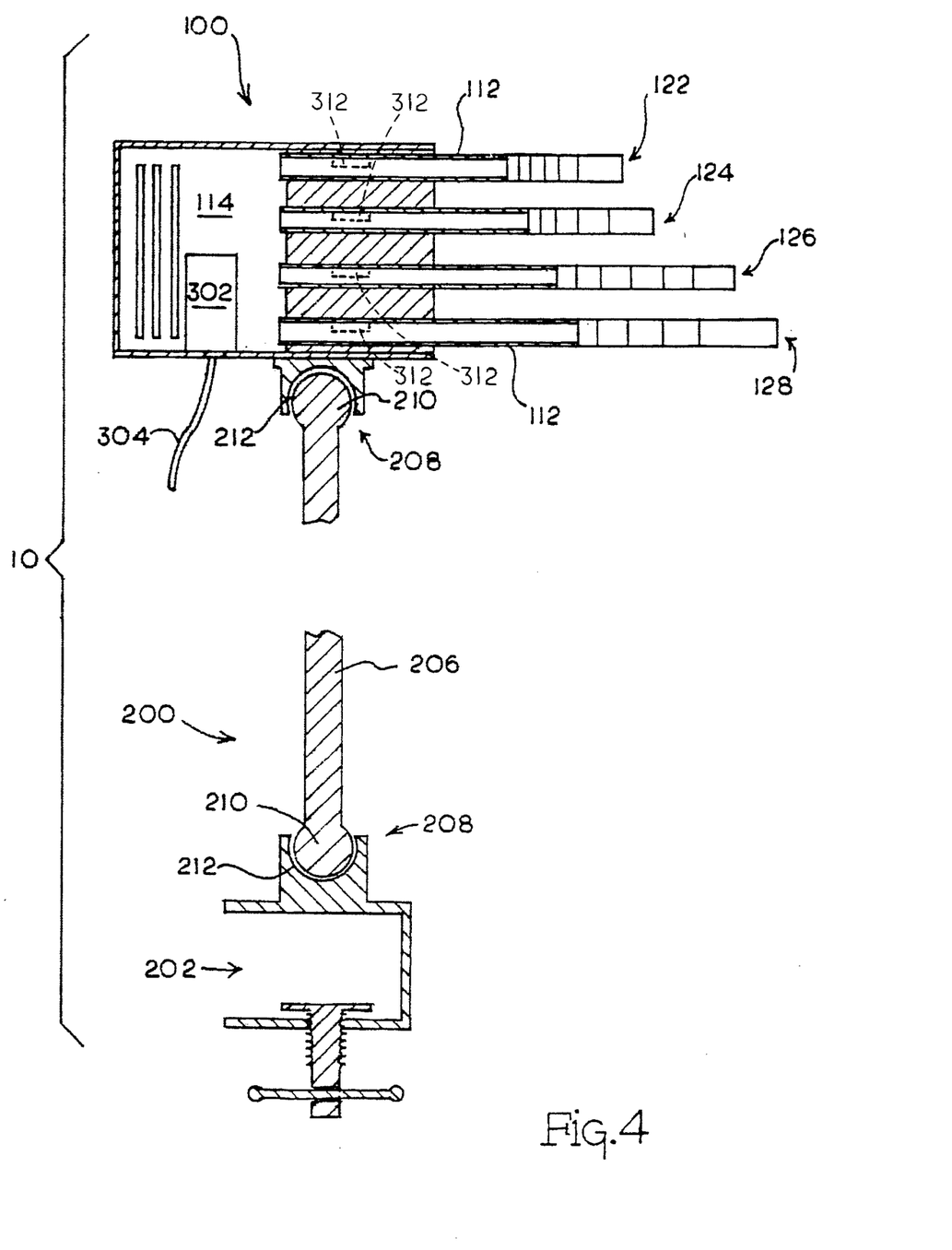
FIG. 4 is a section view of the mouthpiece.

As shown in FIGS. 2–4, the mouthpiece 100 includes a housing 110 which resembles a harmonica. The housing 110 includes a sound chamber 114, the purpose of which is explained below. Mounted within the housing 110 are a plurality of tubular cells 112 which communicate with the sound chamber 114. In the disclosed embodiment, sixty-four cells 112 are arranged in a plurality of rows or tiers 122–128. The top row 122 has 12 cells, the second row 124 has 16 cells, the third row 126 has 16 cells, and the bottom row 128 has 15 cells. The cells 112 are approximately five millimeters in diameter and are spaced approximately five millimeters apart. Each cell functions similar to a key on a keyboard. The user selects a cell 112 by either exhaling or inhaling through the cell 112. The selection of a cell 112 results in a command being sent to the computer analogous to a keystroke on a keyboard. Conventional software running on the computer interprets the command and causes some action to be taken in response to the command.

Mouthpiece 100 has an anthropometric design to enable a user to easily access each cell 112. When viewed from above, each row 122–128 has a generally concave shape, as shown in FIG. 3. The concave shape facilitates the user's access to all of the cells 112. The curve defined by the cells 112 roughly corresponds to the arc made by rotating the user's head. Accordingly, the amount of head/neck movement necessary to select a cell 112 on the concave rows 122–128 is minimized. Movement of the body along the lateral and medial planes is also eliminated so that the user's body remains stationary.

Mouthpiece 100 is also designed so that the user's nose does not interfere with the user's access to any of the cells 112. Each successive row 122–128 of cells 112 from the top row 122 to the bottom row 128 extends slightly farther from the front of the mouthpiece 100 than preceding row. ( See FIG. 4.) By stepping the rows 122–128 in this manner, a user's nose is less likely to be an obstruction when using mouthpiece 100. For example, when a user attempts to blow on a cell 112 located along bottom row 128, the upper rows 122–126 do not block the user's access to the chosen cell 112 because upper rows 122–126 are set back from bottom row 128.

Mouthpiece 100 is mounted adjacent to the computer 12 and supported by an adjustable mount 200. The mount 200 for a conventional desktop computer includes a clamp 202 for securing the mount 200 to a support, a neck 206, and a connector 208 for connecting to the mouthpiece 100. The clamp 202 allows the mouthpiece 100 to be moved between different computers 12. A flexible neck 206 extends upwardly from the clamp 202 and connects to the mouthpiece. The connector 208 may be a universal joint including a ball 210 and a socket 212 that allows movement of the mouthpiece 100 in all three planes. The neck 206 is preferably flexible to allow adjustment.

Figure 7:
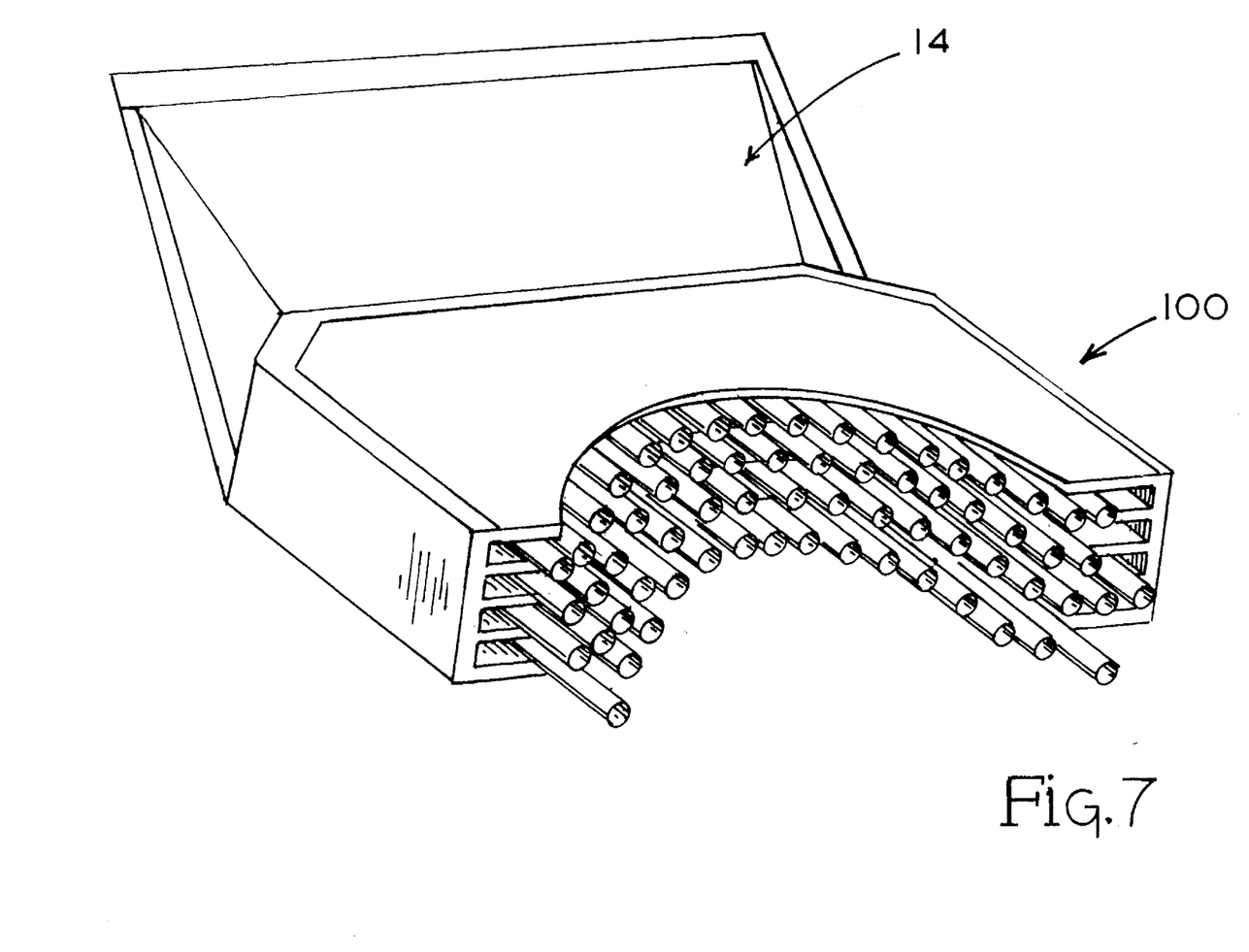
FIG. 7 illustrates a "shoulder top" computer incorporating the input device.
Figure 8:
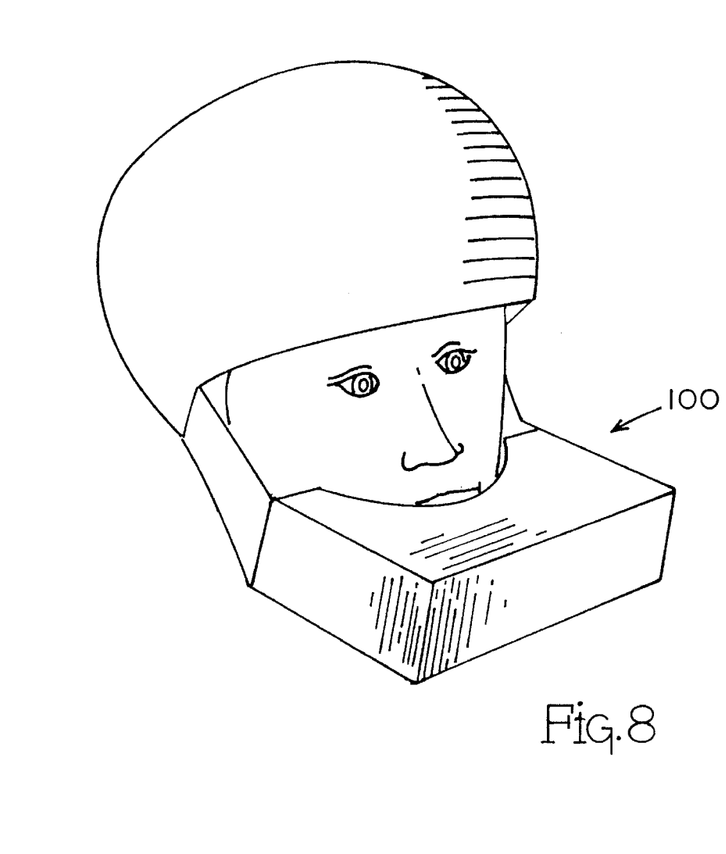
FIG. 8 illustrates a helmet mounted version of the input device.
Figure 9:
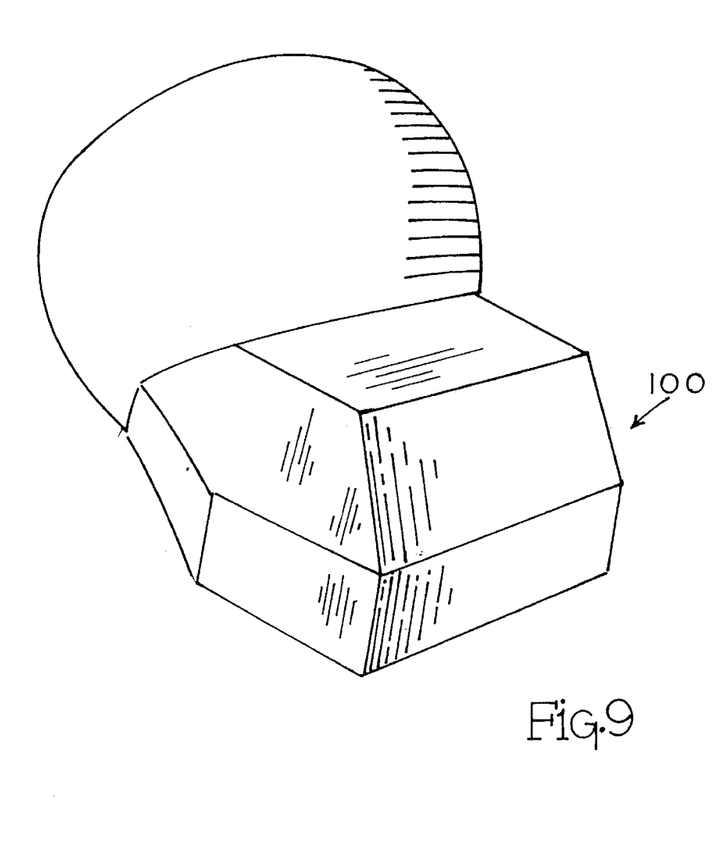
FIG. 9 illustrates the helmet mounted version with a "heads-up" display.

Special mounting systems 200 may also be used for other types of applications. For example, in a "shoulder-top" computer system, the mount may rest on the user's chest and be supported by a neck strap. (See FIG. 7) For use within a helmet, the mount 200 may rest on the shoulders and extend below the chin to support the mouthpiece 100 independently from the helmet. (See FIG. 8)

The user controls the computer 12 by selectively exhaling and inhaling through the individual cells 112 of the mouthpiece 100. The cells 112 are analogous to the keys on a keyboard. That is, the cells 112 enable a user to select and enter commands into computer 200. Like the keys of a keyboard, the cells 112 each correspond to a particular character or command. To select and enter a given character or command, the user selectively exhales or inhales through the cell 112 that corresponds to the chosen character or command. The act of exhaling or inhaling through a cell 112 produces an aspiration signal. For purposes of this application, an aspiration signal is a signal produced by exhaling or inhaling through one of the cells 112 of the mouthpiece 100. The aspiration signal could be pressure, sound, velocity, duration, or other detectable signal. The communications interface 300 transmits the command to the computer 12.

The communications interface 300 includes transducing means for converting aspiration signals into electrical signals that can be interpreted by the computer 12. The transducing means comprises, in the preferred embodiment, a sound transducer 302 such as MIDI (musical instrument digital interface) transducer. Each cell 112 is designed to produce an unique sound. The sound created by exhaling or inhaling on an individual cell 112 has a spectral composition (frequency, pitch, duration, intensity, etc.) which varies in some respect to the spectral composition produced by the other cells 112. In the preferred embodiment, pitch is used to distinguish between the sounds created by the different cells 112.

Since the sound produced by a given cell 112 is a function of its outgoing shape, each cell 112 is capable of producing two different sounds having a unique pitch. The outgoing shape of the cell 112 is different depending upon the direction of the air flow through the cell 112. A first sound is produced when a user exhales through the chosen cell 112, and a second sound is produced when a user inhales through the chosen cell 112. Thus, the mouthpiece 100, which has sixty-four cells 112, is capable of producing one-hundred and twenty-eight different sounds. The unique sounds created by each cell 112 are used to identify which cell 112 a user has chosen and whether the user has inhaled or exhaled through the cell 112.

The sound transducer 302 converts the sounds produced by exhaling or inhaling through cells 112 into distinct digital signals. Sound transducer 302 is mounted within the sound chamber 114. The sounds are converted into electrical signals by the transducer 302. The digital signals generated by the transducer 302 identify the cell 112 chosen by the user and whether the user has exhaled or inhaled through the chosen cell 112. The digital signals are transmitted to the computer 12 by a cable 304. Software running on the computer 12 assigns a command to each cell 112 and uses the digital signals produced by the interface 300 to determine which command a user has chosen.

In an alternate embodiment of input device 10, pressure sensors 312 could be mounted within each cell 112 in place of the sound transducer 302. The pressure transducers 312 are shown in dotted lines in FIG. 4. The pressure transducers 312 detect a change in pressure in the cell 112 when a user exhales or inhales through the cell 112. The change in pressure is converted into a distinct electrical signal by the pressure transducer 312 with the electrical signal being assigned to represent a particular character or command. The pressure sensing transducer 312 sends a digital signals to the computer 12 over a cable 314.

In order to make effective use of the input device 10, the user needs feedback as to whether a cell selection resulted in the desired action. The present invention uses an on-screen keyboard or template 400 to enable the user to visualize the cell selection process. The keys of the on-screen keyboard correspond on a one-to-one basis with the cells 112 of the mouthpiece 110.

Cell selection can be either a two-step process or a one-step process. In a two-step selection process, a desired "key" is first highlighted and then entered after a visual verification of the desired "key" has been made. In the present invention, the two-step process could be implemented by blowing into a cell 112 to select the cell 112 and then inhaling on the cell 112 to enter it. Of course, other sequences are possible, such as blowing once to select a cell 112 and blowing twice in quick succession to enter it. The precise sequence of steps can be varied depending on the physical abilities of the user. A one-step cell selection process could be implemented by blowing on the cell 112 to both select and enter the corresponding command. In the one-step process, verification is made after the cell 112 is entered rather than before. In such case, inhaling on the cell 112 could be used to quickly delete the selection if an erroneous entry is made.

Figure 5:
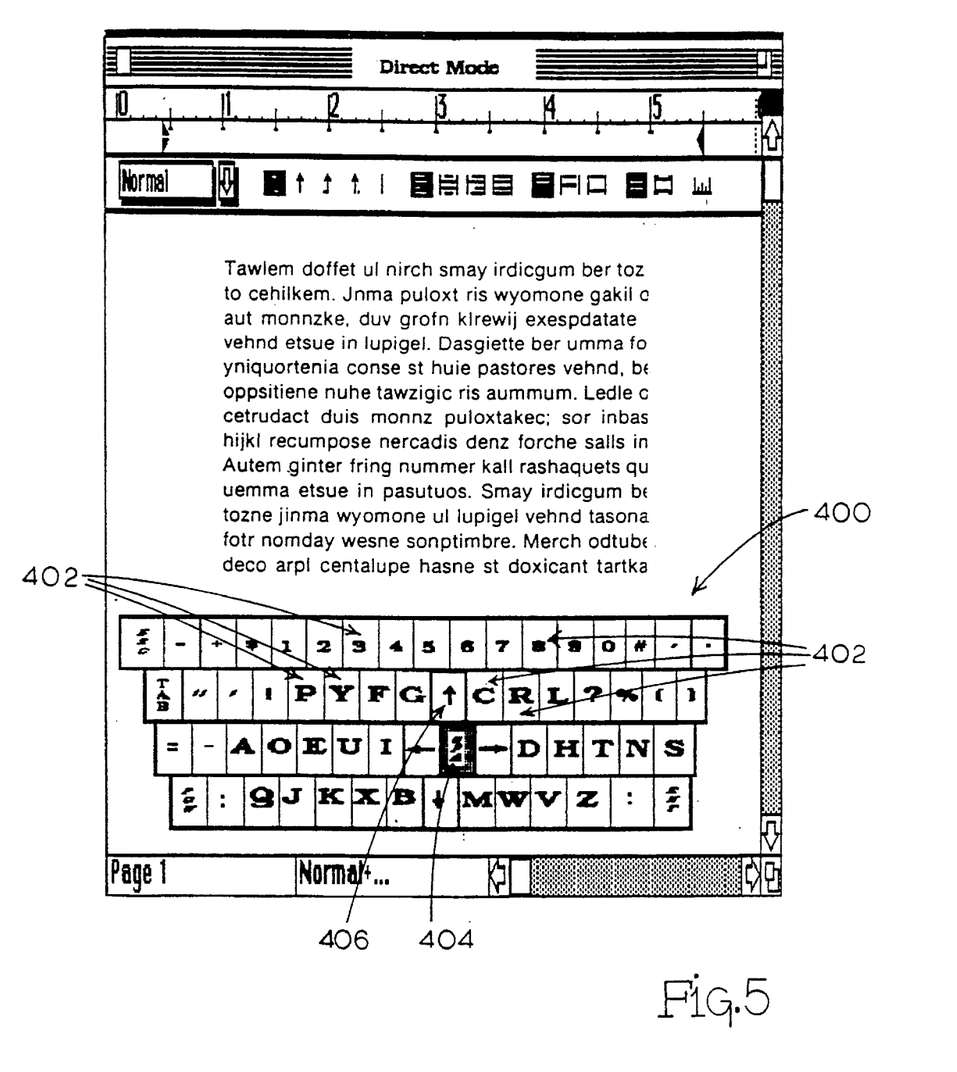
FIG. 5 is a view of the display showing the on-screen keyboard in a direct selection mode.
Figure 6:
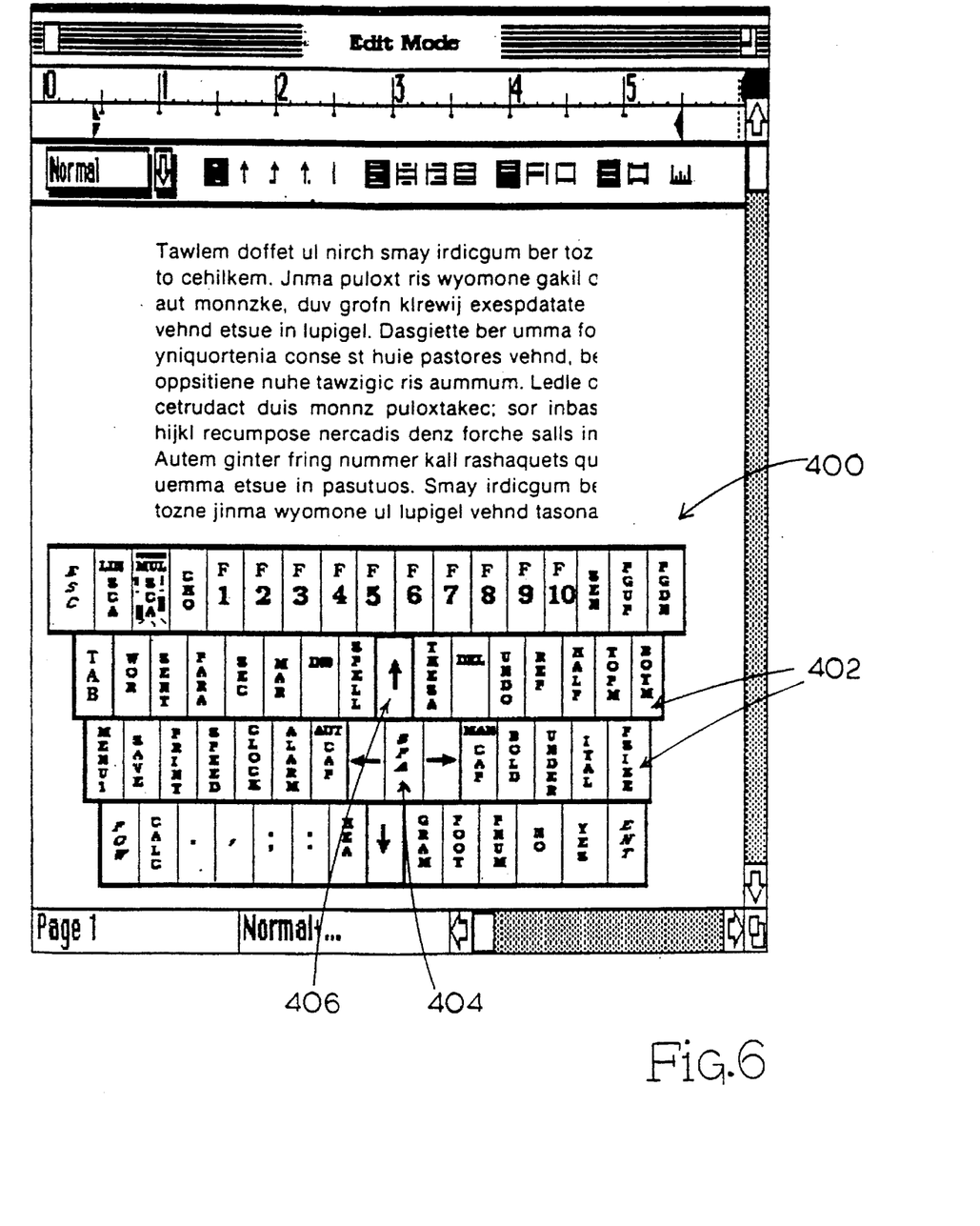
FIG. 6 is a view of the display showing the on-screen keyboard in an edit mode.

Since the input device 10 has only 64 cells, a number of different templates 400 can be used to change the function assigned to each cell 112. Each template includes a plurality of keys 402 which correspond to one of the cells 112 of the mouthpiece. If more than one template 400 is used, one cell 112 is assigned the function of switching modes. The function of the mode cell 112 would not change. The user could then switch between templates 400 depending on the current task. For example, FIGS. 5 and 6 show two different templates 400 used in a word processing program. The template 400 shown in FIG. 5 is used for general typing, while template 400 shown in FIG. 6 is used for editing.

Regardless of the number of templates 400 which are used, certain cells 112 may have dedicated functions which do not change. One example already mentioned is the cell assigned the function of switching modes. This cell is referred to hereinafter as the mode cell. Other dedicated cells include directional arrows for cursor movement and navigation, and an enter cell equivalent to the enter key of a keyboard.

Each template 400 should preferably be laid out in a manner that allows quick selection. Generally, the most frequently used commands are disposed in the middle to allow easier access to those commands. As shown in FIGS. 5 and 6, the keyboard includes a space bar key 404 and directional arrow keys 406 which are located in a center of the template 400. The remaining keys are arranged according to the frequency of use of those keys. Generally, the more frequently a particular character or command is used, the closer it will be to the center. The location of the most frequently used keys in the center of the mouthpiece 100 allows a user to type more efficiently and quickly.

In some cases, it may be desirable to enable the user to customize the keyboard template 400 which is displayed. If so, the software may include a remapping function to allow customized function assignments to be made for each template 400. The user could then reassign the functions to given cells 112 depending upon the user's own preferences and habits.

The templates 400 provide visual feedback to the user during typing or other activities. Other feedback mechanisms indicating which command has been selected can also be used. For example, audible signals corresponding to the different characters and commands could be produced. In addition, a sounding device could announce which character or command had been selected.

In operation, the mouthpiece 100 is attached to the adjustable mount 200 and is plugged into the computer 12. The cable 304 preferably plugs into a standard serial port on the computer 12. Once connected to the computer 12, the input device 10 can be used to interact with the computer 12.

The user selects and enters commands into the computer 12 by selectively exhaling and inhaling through the cells 112. The input device 10 functions in much the same manner as a conventional keyboard or mouse. The user exhales or inhales into the individual cells 112 of the mouthpiece 100 to enter a character or command into computer 12. The interface 300 converts the aspiration signals into electrical signals that can be interpreted by the computer 12.

Software running on the computer 12 allows the user to use other task-oriented application programs such as word processing programs, spread-sheet programs, graphic programs, etc. FIGS. 5 and 6 illustrate how a graphical interface could look for a word processing program. To enter text, a user positions his mouth over a cell 112 that represents a desired character. By blowing once into the cell 112, the character is highlighted. The user then enters the highlighted character into the computer 12 by, for example, blowing twice in quick succession into the cell 112.

Commands can also be entered into computer 12 using the input device 10. The user can enter commands by typing out the commands on a command line as in conventional character-based programs. Alternately, the user can enter commands using a point and shoot approach. Using a point and shoot approach, a cursor is positioned on the screen where commands are graphically represented and a command is selected rather than typed from scratch. For example, the template 400 shown in FIG. 6 is used for entering and editing commands in a word processing program. To position the cursor on the display, directional arrows 406 are provided to enable the user to navigate through the template 400. A user blows into the cells 112 that corresponds to the directional arrows 406 to selectively move the cursor on the display screen.

The user can change the mode by blowing on the mode cell. This changes the function assignment for the cells 112 of the mouthpiece 110. When in the alternate selection mode (See FIG. 6), the cells are assigned functions that correspond to a different set of commands and characters. In the disclosed embodiment, the alternate selection mode is designed for editing in a word processing program. Other specialized selection modes can also be provided for different types of programs.

The input device 10 can also be used in conjunction with a synthesizer to make music. In this application, the input device 10 functions as an electric wind instrument (EWI). That is, the input device 10 can be considered to be an electronic harmonica. The synthesizer would convert the signals from the input device 10 into sounds for the purpose of making music.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A hands-free input device for operating a computer or other electronic device by aspiration, comprising:
   (a) a mouthpiece having a housing that includes a sound chamber;
   (b) a plurality of cells which produce sounds when a user aspirates through the cells, wherein each cell is designed to produce a sound distinct from the sound produced by any other cell, each of said plurality of cells communicating with said sound chamber;
   (c) a sound transducer mounted within said sound chamber for converting the sounds produced by each cell into electrical control signals; and
   (d) communications media connecting the sound transducer to the computer or electronic device for transmitting the control signals to the computer or electronic device to control the same.

2. The input device of claim 1 wherein the input cells are arranged in a plurality of transverse rows.

3. The input device of claim 1 wherein the cells in each row are arranged on the mouthpiece to form a concave shape.

4. The input device of claim 1 wherein each succeeding row of cells extends from the mouthpiece farther than its preceding row of cells.

5. The input device of claim 1 wherein each cell has a different shape to enable the user to distinguish each cell from other cells by tactile sensation.

6. The input device of claim 1 wherein each cell is shaped to produce two distinct sounds depending on the direction of air flow through the cell.

7. A hands-free input device for operating a computer or other electronic device by aspiration, comprising:
   (a) a mouthpiece having a plurality of cells for producing a sound when a user aspirates through each cell, wherein said cells are arranged in a plurality of transverse rows with the cells in each row forming a generally concave shape to facilitate the user's access to said cells with limited head or neck movement;
   (b) sound transducing means for sensing the sound produced by each cell and converting the sound into an electrical control signal; and
   (c) communications media connecting the sound transducing means to a computer or electronic device for transmitting the control signals to the computer or electronic device to control the same.

8. The input device of claim 7 wherein each succeeding row of cells extends from the mouthpiece farther than its preceding row of cells.

9. The input device of claim 7 wherein each cell has a different shape to enable the user to distinguish each cell from other cells by tactile sensation.

10. The input device of claim 7 wherein said mouthpiece comprises a housing that includes a sound chamber, and wherein each of said cells communicates with said sound chamber.

11. The input device of claim 10 wherein the sound transducing means comprises a single sound transducer mounted within said sound chamber.

12. A hands-free method for inputting commands to a computer or other electronic device by aspiration, comprising:
   (a) providing a mouthpiece having a housing that includes a sound chamber and a plurality of air cells communicating with the sound chamber;
   (b) producing distinct sounds by aspirating through the cells;
   (c) detecting the sounds produced by aspirating through the cells with sound transducing means mounted within the mouthpiece;
   (d) converting the sounds to electrical signals with the sound transducing means; and
   (e) transmitting the electrical signals to the electronic device to control the electronic device.

13. The method of claim 12, wherein the sound transducing means comprises a single sound transducer mounted within the sound chamber.

14. The method of claim 13, wherein the air cells are arranged in a plurality of transverse rows on the mouthpiece.

15. The input device of claim 14 wherein the cells in each transverse row are arranged on the mouthpiece to form a concave shape.

16. The input device of claim 15 wherein each succeeding transverse row of air cells extends from the mouthpiece farther than its preceding row of cells.

17. The input device of claim 16 wherein each air cell has a different shape to enable the user to distinguish each air cell from other air cells by tactile sensation.

18. The input device of claim 17 wherein each air cell is shaped to produce two distinct sounds depending on the direction of air flow through the air cell.

* * * * *